US012691080B2

(12) United States Patent
Barnhart

(10) Patent No.: US 12,691,080 B2
(45) Date of Patent: Jul. 28, 2026

(54) FENRETINIDE FORMULATIONS, SYSTEMS INCORPORATING SAME, AND METHODS FOR THEIR USE

(71) Applicant: ARx, LLC, Glen Rock, PA (US)

(72) Inventor: Scott Barnhart, York, PA (US)

(73) Assignee: ARx, LLC, Glen Rock, PA (US)

( * ) Notice: Subject to any disclaimer, the term of this patent is extended or adjusted under 35 U.S.C. 154(b) by 0 days.

(21) Appl. No.: 18/895,267

(22) Filed: Sep. 24, 2024

(65) Prior Publication Data

US 2025/0360090 A1     Nov. 27, 2025

Related U.S. Application Data

(60) Provisional application No. 63/665,239, filed on Jun. 27, 2024, provisional application No. 63/650,010, filed on May 21, 2024.

(51) Int. Cl.
| | |
|---|---|
| *A61K 9/70* | (2006.01) |
| *A61K 31/167* | (2006.01) |
| *A61K 47/10* | (2017.01) |
| *A61K 47/14* | (2017.01) |
| *A61K 47/32* | (2006.01) |
| *A61K 47/38* | (2006.01) |

(52) U.S. Cl.
CPC .......... *A61K 9/7007* (2013.01); *A61K 31/167* (2013.01); *A61K 47/10* (2013.01); *A61K 47/14* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 10,758,619 B2 | 9/2020 | Mallery et al. | |
| 11,679,157 B2 | 6/2023 | Mallery et al. | |
| 2014/0056949 A1 | 2/2014 | Mallery et al. | |
| 2016/0220480 A1 | 8/2016 | Bilal et al. | |
| 2017/0049789 A1* | 2/2017 | Bhalani .................. | A61P 17/00 |
| 2019/0117599 A1 | 4/2019 | Betancourt et al. | |
| 2021/0052732 A1 | 2/2021 | Mallery et al. | |
| 2023/0390190 A1 | 12/2023 | Kakumanu et al. | |

FOREIGN PATENT DOCUMENTS

| | | | | |
|---|---|---|---|---|
| WO | WO-9955312 A2 * | 11/1999 | ........... | A61K 31/137 |
| WO | WO-2012068147 A1 * | 5/2012 | ............. | A61K 31/07 |
| WO | WO 2017/147169 A1 | 8/2017 | | |

OTHER PUBLICATIONS

Melis et al. (Fenertinide reduces intestinal Mucin-2 Positive Goblet cells in chronic alcohol abuse, Parhamcology, 2022) (Year: 2022).*

Flugge et al. "Detection of Oral Squamous Cell Carcinoma in Clinical Photographs Using a Vision Transformer," Nature Sci. Reports 13:2296 (2023) https://doi.org/10/1038/s41598-023-29204-9.

Han et al., "Fenretinide Perturbs Focal Adhesion Kinase in Premalignant and Malignant Human Oral Keratinocytes. Fenretinide's Chemopreventative Mechanisms Include ECM Interactions," *Cancer Prev. Res.* 8(5) 419-30 (May 2015) https://pubmed.ncbi.nlm.nih.gov/25712051/.

Holpuch et al., "Optimizing Therapeutic Efficacy of Chemopreventive Agents: A Critical Review of Delivery Strategies in Oral Cancer Chemoprevention Clinical Trials," *J. Carcinog.* 10(23) 1-12 (2011).

Holpuch et al., "Evaluation of a Mucoadhesive Fenretinide Patch for Local Intraoral Delivery: A Strategy to Reintroduce Fenretinide for Oral Cancer Chemoprevention," *Carcinogenesis* 33(5) 1098-1105 (2012). https://academic.oup.com/carcin/articles/33/5/1098/2463817.

Johnson et al., "Head and neck squamous cell carcinoma," *Nat Rev Dis Primers.* Author manuscript; available in PMC Mar. 10, 2021 https://www.ncbi.nlm.nih.gov/pmc/articles/PMC7944998/pdf/nlhms-1667936.pdf.

Kansara et al., Premalignant Lesions of the Oral Mucosa (StatPearls, May 23, 2023) accessed at https://www.ncbi.nlm.nih.gov/books/NBK572155/.

Lodi et al., "Interventions for Treating Oral Leukoplakia to Prevent Oral Cancer (Review)" *Cochrane Database of Sys. Revs.* 2016 (7) Art. No. CD001829; https://www.cochranelibrary.com/cdsr/doi/10.1002/14651858.CD001829.pub4/full.

Mallery et al., "Effects of Human Oral Mucosal Tissue, Saliva, and Oral Microflora on Intraoral Metabolism and Bioactivation of Black Raspberry Anthocyanins," Cancer Prev. Res. 4(8) 1209-21 (2011) https://www.ncbi.nlm.nih.gov/pmc/articles/PMC3151333.

Mallery et al., "Clinical and Biochemical Studies Support Smokeless Tobacco's Carcinogenic Potential in the Human Oral Cavity," *Cancer Prev. Res.* 7(1) 23-32 (2013) https://ncbi.nlm.nih.gov/pmc/articles/PMC3892990.

Mallery et al. "Benefits of Multifaceted Chemopreventatives in the Suppression of the Oral Squamous Cell Carcinoma (OSCC) Tumorigenic Phenotype," *Cancer Prev. Res.* 10(a) 76-88 (Jan. 2017) https://aacrioumals.org/cancerpreventionresearch/article/10/1/76/99952/Benefits-of-Multifaceted-Chemopreventives-in-the Mallery et al., "Fenretinide, Tocilizumab, and Reparixin Provide Multifaceted Disruption of Oral Squamous Cell Carcinoma Stem Cell Properties: Implications for Tertiary Chemoprevention," *Mol. Cancer Ther.* 18(12) 2308-2320 (2019) https://doi.org/10.1158/1535-7163.MCT-19-0361.

Mohrbacher et al., "Phase I Study of Fenretinide Delivered Intravenously in Patients with Relapsed or Refractory Hematologic Malignancies: A California Cancer Consortium Trial," *Clin. Cancer Res.* 23(16) 4550-4555 (2017).

Nieto et al., "Microencapsulation of amorphous solid dispersions of fenretinide enhances drug solubility and release from PLGA in vitro and in vivo," *Int'l J. Pharmaceutics* 586 (No. 119475) (Aug. 30, 2020) https://www.sciencedirect.com/science/articles/abs/pll/S0378517320304592.

(Continued)

*Primary Examiner* — Melissa S Mercier

(74) *Attorney, Agent, or Firm* — Green, Griffith & Associates LLP

(57) ABSTRACT

Formulations comprising fenretinide, methods for the preparation of such formulations, systems (e.g., patches) comprising such formulations, as well as for their use as a secondary chemopreventive for precancerous lesions in the stratified squamous epithelium of mucosal tissue.

16 Claims, 2 Drawing Sheets

(56) References Cited

OTHER PUBLICATIONS

Wang et al., "Fenretinide Combines Pertubation of Signaling Kinases, Cell-extracellular matrix interactions and Matrix Metalloproteinase Activation to Inhbiti Invasion in Oral Squamous Cell Carcinoma Cells," *Carcinogenesis* 43(9) 851-864 (2022) https:doi.org/10.1093/carcin/bgac070.

Wu et al., "Mucoadhesive Fenretinide Patches for Site-Specific Chemoprevention of Oral Cancer: Enhancement of Oral Mucosal Permeation of Fenretinide by Coincorporation of Propylene Glycol and Menthol," *Mol. Pharmaceutics* 9:937-945 (2012) https://pubs.acs.org/doi/full/10.1021/mp200655k.

Desai et al., "Development and In Vitro-In Vivo Evaluation of Fenretinide-Loaded Oral Mucoadhesive Patches for Site-Specific Chemoprevention of Oral Cancer," *Pharm. Res.*, Author manuscript; available in PMC Oct. 1, 2012, pp. 1-21, https://pmc.ncbl.nlm.nih.gov/articles/PMC3171589/.

Ledet et al., "Preparation and In Vitro Evaluation of Hydrophilic Fenretinide Nanoparticles," Int. J. Pharm., Author manuscript, available in PMC Feb. 20, 2016, pp. 1-23, https://pmc.ncbi.nlm.nih.gov/articles/PMC4346548/pdf/nihms-651756/.

United States Patent and Trademark Office, International Search Report and Written Opinion issued in International Patent Application No. PCT/US2025/026312, Jul. 9, 2025.

* cited by examiner

FENRETINIDE FORMULATIONS, SYSTEMS INCORPORATING SAME, AND METHODS FOR THEIR USE

CROSS-REFERENCE TO RELATED APPLICATIONS

This application claims the benefit of U.S. Provisional Patent Application No. 63/665,239 filed on Jun. 27, 2024, and U.S. Provisional Patent Application No. 63/650,010 filed on May 21, 2024, the disclosures of which are incorporated by reference in their entireties herein.

STATEMENT REGARDING FEDERALLY SPONSORED RESEARCH

This invention was made with government support under Federal Grant R01 CA227273 awarded by the National Cancer Institute of the National Institutes of Health, U.S. Department of Health and Human Services. The U.S. government has certain rights in the invention.

BRIEF SUMMARY OF THE INVENTION

The present invention generally relates to formulations comprising a retinoid, e.g., fenretinide, and methods for the preparation of such formulations, systems (e.g., patches) comprising such formulations, as well as for their use as a secondary chemopreventive for precancerous lesions in the stratified squamous epithelium.

BACKGROUND OF THE INVENTION

Stratified squamous epithelial cells (SSECs), which collectively comprise the body's integument and mucosal surface covering, are found in key barrier locations in the body, including in the oral cavity, the oropharynx, the larynx, the esophagus, the vagina and anal canal, as well as in the cervix and outer layer of the skin (i.e., the epidermis).

SSECs are susceptible to the development of precancerous lesions and carcinomas, such as squamous cell carcinomas (SCCs), likely reflective of both their location and exposure to carcinogens.

SCCs are the most common malignancies that arise in the head and neck, developing in the stratified squamous epithelium of the oral cavity, oropharynx and larynx (head and neck SCC, or HNSCC). HNSCC is the sixth most common cancer worldwide, with 890,000 new cases and 450,000 deaths in 2018. The incidence of HNSCC continues to rise, which largely reflects oncogenic HPV oropharyngeal development in the U.S, and is anticipated to rise by 30% (that is, 1.08 million new cases annually) by 2030.

Of the locations associated with HNSCC, the oral cavity is the most frequently afflicted, with a reported SCC incidence of 377,713, and 117,757 deaths, in 2020. The five-year survival rate is over 80% if treatment is commenced in the early stages, but decreases to <30% for advanced disease.

SCCs do not develop de novo, but arise from precancerous lesions which develop upon exposure to carcinogens. For example, oral squamous cell carcinomas (OSCCs) arise from precancerous oral lesions that develop in the surface stratified squamous epithelium. While these lesions can develop anywhere within the oral cavity, three primary high risk "pooling" sites are recognized: the anterior floor of mouth and ventral tongue; the posterior lateral tongue; and the retromolar trigone-anterior tonsillar pillar.

Established risk factors associated with the development of these precancerous lesions in the oral cavity, and thus OSCC, include tobacco use, oncogenic HPV subtypes (most commonly HPV 16 for oral lesions), use of betel quid and gutka, immunosuppression (either iatrogenic or disease associated, e.g., HIV), UV radiation (actinic cheilitis (lip)), genetic syndromes associated with DNA repair deficits, e.g., Fanconi anemia, Dyskeratosis congenital. There also is a highly aggressive form of precancerous oral epithelial disease, i.e., proliferative verrucous leukoplakia, which is characterized by multifocal lesions and increased rate of malignant transformation to OSCC. Due to its capacity to facilitate carcinogen uptake and directly induce cytochrome P450 enzymes, alcohol has been discussed as a plausible OSCC co-factor, particularly for burnt tobacco products.

Oral epithelial lesions include leukoplakia, erythroplakia, erythroleukoplakia, oral submucous fibrosis, oral lichen planus, actinic cheilitis and palatal lesions. These lesions may be clinically identifiable by their color, adherent nature and crisply delineated clinical margins. Leukoplakia are white patches that cannot be wiped away and cannot be characterized clinically or pathologically as any other condition. While many leukoplakias are benign, some may show signs of dysplasia (abnormal cell growth) upon microscopic examination, and a subset may progress to cancer. Erythroplakia are less common than leukoplakias and appear as a red patch in the oral cavity. Erythroplakia often present a greater potential for malignancy compared to leukoplakia, with a significant portion of lesions showing dysplasia or carcinoma upon biopsy. Erythroleukoplakia (which also may be referred to as speckled leukoplakia, appears as a mix of red and white areas. Like erythroplakia, this type of lesion has a higher risk of cancerous transformation. Oral submucous fibrosis, particularly prevalent in the Indian subcontinent, is associated with the chewing of areca nut (often as a component of betel quid). Oral submucous fibrosis is characterized by progressive fibrosis of the submucosal tissue, leading to stiffness and reduced mouth opening, and has a potential for malignant transformation. Oral lichen planus, while primarily considered a chronic inflammatory condition, some forms, especially the erosive type, are associated with a slightly increased risk of malignancy. Actinic cheilitis is a precancerous condition of the lips that is associated with prolonged sun exposure. It mainly affects the lower lip and appears as a scaly or rough patch. Palatal lesions are lesions found on the palate of individuals who practice reverse smoking (when the lit end of the cigarette or cigar is placed inside the mouth), and have a potential for malignant transformation.

Early identification of these lesions, and prompt therapy thereafter, are critical to optimal patient outcomes.

Therapies for these oral epithelial lesions that are determined to be precancerous (which also are referred to as oral intraepithelial neoplasias, or OINs) include excisional biopsy (enabling microscopic assessment of the lesional tissue) or laser ablation, topical steroids, and the oral administration of non-steroidal anti-inflammatory drugs and retinoids, although the overall quality of evidence as to the effectiveness of non-surgical options, at least against leukoplakia, has been characterized as being very low. While a variety of other treatments have been evaluated, none of these strategies has been wholly successful. Holpuch et al., "Optimizing Therapeutic Efficacy of Chemopreventive Agents: A Critical Review of Delivery Strategies in Oral Cancer Chemoprevention Clinical Trials," *J. Carcinog.* 10(23) 1-12 (2011). The repurposing of certain systemically administered drugs developed for other diseases also has been attempted (e.g., metformin, NCT 02581137, and pembrolizumab, NCT 02882282); Lodi et al. "Interventions for Treating Oral Leukoplakia to Prevent Oral Cancer (Review)" *Cochrane Database of Sys. Revs.* 2016 (7) Art. No. CD001829. Alternatively, or as an adjunct, locally-applied therapies, such as radiation or photodynamic therapy, have been used. However, even with such therapies, many of the precancerous lesions reoccur. Further, and in the case of OSCC, even if surgical intervention is curative, facial structures vital for function and esthetics are commonly sacrificed.

Systemically-delivered chemopreventatives should conceptually provide therapy to all such precancerous lesions, potentially precluding the need for surgical intervention. However, bioavailability challenges and unacceptable drug-related systemic toxicities have generated disappointing outcomes. Further, considering the likelihood of stem cell involvement, oral cancer chemoprevention will likely be necessary for the lifetime of the patient.

While mucous in the oral cavity (and in other mucosal tissues) can impede local drug delivery, chemopreventive formulations specifically designed to locally deliver a particular drug (i.e., N-(4-hydroxyphenyl) retinamide, more commonly referred to as fenretinide) to mucosal tissues in the oral cavity have been developed to address precancerous lesions therein. See WO2012/068147A1.

Studies to assess the effects of oral mucosal patch-delivered fenretinide demonstrated a marked pharmacologic advantage (e.g., treatment relevant drug levels within the oral epithelium in the absence of any systemically detectable drug), with the fenretinide patch-treated oral mucosa exhibiting a clinically normal appearance and exhibiting a modest increase in keratinization. Further, a dose-related response was noted in the surface epithelium, i.e., epithelial proliferation (Ki-67 indices) was significantly reduced in epithelium, with higher fenretinide levels (>5 µM). Fenretinide levels lower than 5 µM were associated with differentiation effects as indicated by reduced proliferation and increased levels of transglutaminase 1 (a key enzyme in the formation of the keratinocyte envelope). Lower fenretinide levels also demonstrated an increase in the Phase II enzyme, UGT1A1. Holpuch et al. "Evaluation of a Mucoadhesive Fenretinide Patch for Local Intraoral Delivery: A Strategy to Reintroduce Fenretinide for Oral Cancer Chemoprevention," *Carcinogenesis* 33(5) 1098-1105 (2012).

Additional translational studies in premalignant and malignant human oral keratinocytes have demonstrated additional fenretinide mechanisms of action that include disruption of proinflammatory and proliferative pathways that are associated with malignant progression. Han et al., "Fenretinide Perturbs Focal Adhesion Kinase in Premalignant and Malignant Human Oral Keratinocytes. Fenretinide's Chemopreventive Mechanisms Include ECM Interactions," *Cancer Prev. Res.* 8(5): 419-30 (May 2015); Mallery et al. "Benefits of Multifaceted Chemopreventatives in the Suppression of the Oral Squamous Cell Carcinoma (OSCC) Tumorigenic Phenotype," *Cancer Prev. Res.* 10(a): 76-88 (January 2017); Wang, "Fenretinide Combines Perturbation of Signaling Kinases, Cell-extracellular Matrix Interactions and Matrix Metalloproteinase Activation to Inhibit Invasion in Oral Squamous Cell Carcinoma Cells," *Carcinogenesis* 43; 851-864 (2022); Mallery et al., "Fenretinide, Tocilizumab, and Reparixin Provide Multifaceted Disruption of Oral Squamous Cell Carcinoma Stem Cell Properties: Implications for Tertiary Chemoprevention," *Mol. Cancer Ther.* 18(12): 2308-2320 (2019). Collectively, these studies imply that fenretinide can function as a small molecule protein inhibitor for kinases that are frequently aberrantly upregulated during malignant transformation.

Despite these advances, there remains a need for improved formulations of fenretinide, as well as methods of preparing same, that may be used as a secondary chemopreventive for precancerous lesions in the stratified squamous epithelium.

SUMMARY OF THE INVENTION

In one aspect, the present invention provides a formulation comprising, consisting essentially of, or consisting of, fenretinide and a cellulose that is relatively highly soluble in both water and polar organic solvents (acetone, ethanol and isopropanol). In all aspects of the inventive formulations, the cellulose is desirably hydroxypropyl cellulose (HPC).

Other aspects of the invention contemplate including the inventive formulations described herein in a mucoadhesive delivery system. Such systems, which also may be referred to as a patch, comprise an inventive formulation as described herein and a backing layer, and are designed to deliver the fenretinide transmucosally from the formulation to provide for the treatment of a precancerous lesion in the stratified squamous epithelium.

In related aspects, the invention provides methods for the treatment of a patient afflicted with precancerous lesions in the stratified squamous epithelium of mucosal tissue using the inventive formulations or systems.

Methods for the preparation of the inventive formulations and systems also are contemplated by the present invention.

Other inventive formulations, systems and methods, and features and advantages of those and of the various aspects of the present invention, will be apparent upon review of the following drawings and detailed description of the invention, and form part of the description of the present invention.

DETAILED DESCRIPTION OF THE INVENTION

Figure 1A:
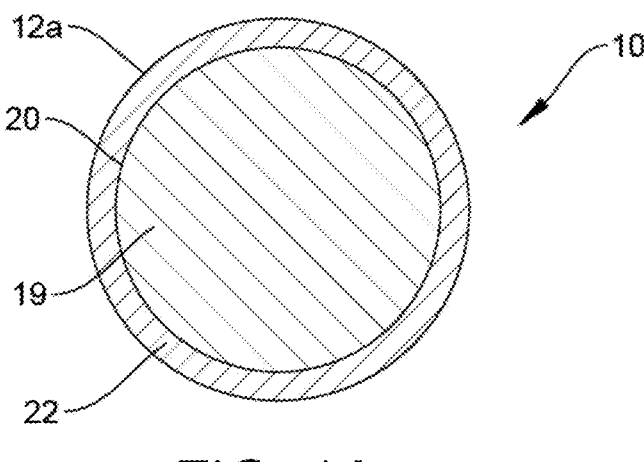
FIGS. 1A and 2A, 1B and 2B, and 1C and 2C, are illustrative of three variations of one aspect of the present invention in the form of a transmucosal delivery system, showing a mucoadhesive formulation layer (in this illustration, a thin film which includes fenretinide as the active pharmaceutical ingredient) and a backing layer attached thereto, wherein the exposed side of the formulation layer is to be applied onto a precancerous lesion in the stratified squamous epithelium.

The present invention provides formulations, as well as systems comprising and therapeutic methods of using such formulations, for the transmucosal delivery of fenretinide to treat a patient afflicted with a precancerous lesion in the stratified squamous epithelium, which exhibit advantages relative to known fenretinide-containing transmucosal formulations, systems and therapeutic methods.

In one aspect, the present invention provides a formulation comprising, consisting essentially of, or consisting of, fenretinide and a cellulose that is relatively highly soluble in both water and polar organic solvents, i.e., acetone, ethanol, isopropanol and mixtures thereof.

A related aspect of the invention provides a formulation comprising, consisting essentially of, or consisting of, fenretinide, a permeation enhancer, and a cellulose that is relatively highly soluble in both water and polar organic solvents, such as acetone, ethanol and isopropanol.

The present invention contemplates the inclusion of fenretinide (N-(4-hydroxyphenyl)retinamide) as the active pharmaceutical ingredient (API). Fenretinide is a synthetic retinoid derivative developed in the 1970s, and is related to Vitamin A. Soluble in most organic solvents, fats, oils and aqueous micellar solutions, fenretinide is sparingly soluble in water (13 nmol/L pH 6.5) and also is sensitive to light.

Fenretinide provides a therapeutic function in connection with the present invention, for example, as a chemopreventive agent for precancerous lesions in mucosal stratified squamous epithelium, such lesions including leukoplakia, erythroplakia, erythroleukoplakia, oral submucous fibrosis, oral lichen planus, actinic cheilitis and palatal lesions. Thus, in the context of the invention, the inventive fenretinide-containing formulations are effective, for a particular precancerous lesion, in: (a) causing regression of the lesion, (b) modulating the progression of the lesion into carcinoma, or (c) preventing the progression of the lesion into carcinoma. These aspects of the invention will be further described herein.

Aspects of the invention provide for the inclusion of fenretinide in formulations in a relatively wide range of concentrations, and advantageously in relatively high fenretinide concentrations. Desirably, and in certain aspects of the invention, fenretinide is present in formulations in amounts ranging from about 1, 2, 3, 4, 5, 6, 7, 8, 9, 10, 11 or 12 wt. % up to about 14, 15, 16, 17, 18, 19 or 20 wt. %, desirably from about 10 wt. % to about 20 wt. %, more desirably from about 12 wt. % to about 18 wt. %, even more desirably from about 14 to about 16 wt. %, and preferably about 15 wt. %.

In other aspects of the invention, it is desirable that the inventive formulations, which are preferably provided as individual dosage forms, provide for the inclusion of fenretinide in relatively significant amounts. Such amounts range from about 10 μg, 15 μg, 20 μg, 50 μg, 100 μg, 500 μg, 1 mg, 2, mg, 3 mg, 4 mg, 5 mg, 6 mg, 7 mg, 8 mg, 9 mg, 10 mg, 11 mg, 12 mg, 13 mg, 14 mg or 15 mg up to about 20, 21, 22, 23, 24 or 25 mg. The amount of fenretinide in a finished dosage form based on the surface area of the formulation film to be applied onto a precancerous lesion (as will be described in more detail herein) may range from about 0.1, 0.2, 0.3, 0.4, 0.5, 0.6, 0.7, 0.8, 0.9, 1, 1.1, 1.2, 1.3, 1.4, 1.5, 1.6, or 1.7 mg fenretinide/cm$^2$ up to about 2, 2.1, 2.2, 2.3, 2.4, 2.5, 2.6, 2.7, 2.8, 2.9 3, 3.1, 3.2, 3.3, 3.4, 3.5, 4, 4.5, or 5 mg fenretinide/cm$^2$, desirably from about 1 to about 3 mg fenretinide/cm$^2$, more desirably from about 1.5 to about 2.5 mg fenretinide/cm$^2$, even more desirably from about 1.7 to about 2 mg fenretinide/cm$^2$, and most desirably about 1.9 mg fenretinide/cm$^2$.

The formulation aspects of the present invention further contemplate the inclusion of a cellulose that is relatively highly soluble in both water and the polar organic solvents acetone, ethanol, isopropanol and/or mixtures thereof. It was unexpectedly discovered that this dual solubility is advantageous in several respects. For example, in the preparation of the inventive formulations, it was found that the API, cellulose and all other formulation ingredients could be uniformly distributed in the formulation mixture (which mixture is desirably in the form of a solution wherein all ingredients are dissolved in a polar organic solvent (desirably a combination of two or more of acetone, ethanol, or isopropanol, and more desirably ethanol and isopropanol in equal proportions) as further described herein) used to provide the relatively thin formulation film (the film formed, preferably, via casting and drying (which volatilizes the aforesaid polar organic solvent(s)) as will be described in more detail herein), as well as in the individual dosage forms prepared from the thin formulation film. In addition, the water-soluble property of the cellulose enabled the formulation film, in the finished dosage form, to become hydrated and adhere to the mucosal (water-containing) tissue. It was further found that the inclusion of such a cellulose assists in providing desirable flexibility in the formulation film, which enables the film to be converted into finished dosage forms, and the individual finished dosage forms to be handled and used by a healthcare provider, without physical damage, e.g., cracking, or breaking into at least two pieces, to the film alone or the film in the finished dosage form.

In certain aspects of the invention, it is desirable that this cellulose is present in inventive formulations in amounts ranging from about 1, 2, 3, 4, 5, 6, 7, 8, 9, 10, 11, 12, 13, 14 or 15 wt. % up to about 20, 21, 22, 23, 24, 25, 26, 27, 28, 29, 30, 35 or 40 wt. %, and desirably from about 10 wt. % to about 35 wt. %, more desirably from about 15 wt. % to about 30 wt. %, and most desirably from about 20 wt. % to about 25 wt. %.

Desirably, the cellulose excipient is HPC. Of the various grades of HPC available, it was found that HPCs (one HPC or a mixture of a plurality of HPCs) each having a weight average molecular weight (Mw) below about 400,000 were desirable, as HPCs when included in the desired amounts and having a relatively higher Mw provided formulations with viscosities that were too high to provide for relative ease of casting and film formation. A single HPC, or a plurality of HPCs, having a (n) (average, if more than one HPC) Mw of about 40,000, 50,000, 60,000, 70,000 80,000, 90,000, 100,000, 110,000, 120,000, 130,000, 140,000, 150, 000, 175,000, 200,000, 225,000, 250,000, 275,000, 300,000, 325,000, 350,000, 375,000 or about 400,000, are more desirable, with a single HPC, or a plurality of HPCs, having a (n) average Mw of from about 40,000, 50,000, 60,000, 70,000 80,000, 90,000, 100,000, 110,000, 120,000, 130,000, 140,000, 150,000, 175,000, 200,000, or 225,000 up to about 275,000, 300,000, 325,000, 350,000, 375,000 or about 400, 000, and more preferably from about 200,000 to about 300,000, and even more preferably from about 225,000 to about 275,000. These HPCs (desirably pharmaceutical grade) also may have a particle size of about 99.9% through 250 μm, <90% through 177 μm, and <80% through 149 μm, and further may comprise about 50% to about 80% hydroxypropoxy groups. Illustrative of HPCs useful in the various aspects of the invention (alone or in combination) include the EL (about 40,000 Mw), E (about 80,000 Mw), L (about 95,000 Mw), J (about 140,000 Mw) and G (about 370,000 Mw) grades of HPC (each of which may have a "F" after each grade to designate a pharmaceutical-suitable ingredient) marketed under the Klucel™ trademark (Ashland Inc., Kentucky, US).

Accordingly, all aspects of the inventive formulations desirably contain very limited, if any, amounts of cellulose-based excipients that are sparingly, or insoluble, in water, such as microcrystalline cellulose (MCC) and ethyl-containing celluloses (e.g., ethyl cellulose (EC), hydroxyethyl cellulose (HEC)), nor cellulose-based excipients that exhibit very limited solubility in polar organic solvents, such as, for example, methyl-containing celluloses (e.g., hydroxypropyl methylcellulose (HPMC), carboxymethylcellulose (CMC), methylcellulose (MC)). Such excipients will not completely dissolve in the formulation and/or may provide the formulation with an undesirable gummy consistency, as the formulation used to prepare the formulation film is desirably a solution (as will be further described herein). If present, these excipients are limited to amounts ranging from about 0.001 wt. % to about 2, 1, 0.5, or 0.01 wt. %. Desirably, the inventive formulations have no detectable amounts of such excipients therein.

All aspects of the inventive formulations may further contain very limited, if any, polymers and/or copolymers of (meth)acrylic acid, (meth)acrylate and/or esters thereof. It was discovered that the inclusion of these excipients contributed to undesirable properties in a known fenretinide-containing mucoadhesive dosage form. By way of illustration, a formulation film which included such excipients was found to be excessively brittle, and easily damaged when converted into finished dosage form (e.g., via die cutting) and when such finished dosage form is handled by a healthcare provider (in both scenarios, the film is susceptible to physical damage in the form of cracking, breaking into two or more pieces, and/or chipping). Illustrative of such undesirable copolymers include, without limitation, copolymers marketed under the Eudragit® trademark (Evonik Industries AG, Essen, Germany), such as copolymers of methacrylic acid and methyl methacrylate (e.g., Eudragit® L and S); copolymers of acrylic acid and (meth)acrylic esters (e.g., Eudragit® RL and RS, such as amino methacrylate copolymer (Eudragit® RL PO)); copolymers of dimethylaminoethyl methacrylate, butyl methacrylate, and ethyl acrylate (e.g., dimethylaminoethyl methacrylate-copolymer (Eudragit® E PO)), and copolymers of ethyl acrylate, methyl methacrylate, and methacrylic acid, (e.g., poly(ethyl acrylate-co-methyl methacrylate) 2:1 (Eudragit® NM30D)). If present, these excipients are limited to an amount ranging from about 0.001 wt. % to about 2, 1, 0.5, or 0.01 wt. %. Desirably, the formulations have no detectable amount of these excipients.

Certain formulation aspects of the present invention further contemplate the inclusion of a permeation enhancer. Permeation enhancers may assist in providing an enhanced delivery profile, and more efficient delivery, of the API. Illustrative of the permeation enhancers useful in various aspects of the present invention include propylene glycol (PG), terpenoids and/or terpenes (such as menthol, D-limonene, geraniol, nerolidol), and mixtures thereof. The terpenoids and/or terpenes desirably may be menthol, with the preferred permeation enhancer comprising, consisting essentially of, or consisting of PG and a terpenoid and/or terpenes and, more preferably, PG and menthol.

The aforedescribed permeation enhancer desirably may be present in the various aspects of the inventive formulations from about 10, 11, 12, 13, 14, 15, 16, 17, 18, 19 or 20 wt. % up to about 25, 26, 27, 28, 29, 30 or 35 wt. %, more desirably from about 15 wt. % to about 25 wt. %, and even more desirably from about 20 wt. % to about 25 wt. %.

In aspects of the invention wherein the permeation enhancer comprises, consists essentially of, or consists of, PG and a terpenoid and/or terpene (and more preferably menthol), the PG is desirably present in an amount ranging from about 1, 2, 3, 4, 5 or 6 wt. % up to about 8, 9, 10, 11, 12, 13, 14 or 15 wt. %, desirably from about 5 wt. % to about 10 wt. %, more desirably from about 6 wt. % to about 9 wt. %, and most desirably about 7 wt. %, while the terpenoid and/or terpene (desirably menthol) may be present in an amount ranging from about 5, 6, 7, 8, 9, 10, 11 or 12 wt. % up to about 17, 18, 19, 20, 21, 22, 23, 24 or 25 wt. %, desirably from about 10 wt. % to about 20 wt. %, even more desirably from about 12 wt. % to about 18 wt. %, and most desirably about 15 wt. %.

In related aspects of the invention wherein the permeation enhancer comprises, consists essentially of, or consists of, PG and a terpenoid and/or terpene (and more preferably menthol), the weight ratio of PG to a terpenoid and/or terpene (preferably, menthol) also may range from about 1:1.5 to about 1:3, desirably from about 1:2 to about 1.25, and more desirably about 1:2, based on the total weight of the two permeation enhancers. Additional aspects of the present invention contemplate the permeation enhancers being included therein in both the aforedescribed weight ratios and weight percentages.

Another aspect of the invention provides a formulation comprising, consisting essentially of, or consisting of, fenretinide, a povidone, and HPC. Povidone, also known as polyvinylpyrrolidone (PVP), may perform one or more of several functions in the inventive formulations, including, without limitation, assisting in the solubilization of the API, improving the physical properties of the formulation (e.g., adhesion), facilitating permeation of the API through the mucosa, and stabilizing the API in the formulation.

However, in aspects of the invention wherein povidone is included in the formulations, it was discovered that the amount of povidone should be limited to no more than about 30 wt. %, as formulation films (and dosage forms prepared therefrom) comprising povidone in excess of this amount were found to exhibit undesirable properties. In this regard, and if present, povidone may be included in the inventive formulations at from about 1, 5, 6, 7, 8, 9, 10, 11, 12, 13, 14, 15, 16, 17, 18, 19, or 20 wt. % up to about 25, 26, 27, 28, 29 or 30 wt. %, desirably from about 15 wt. % to about 30 wt. %, and more desirably from about 20 wt. % to about 25 wt. %.

The fenretinide-containing formulation may further, and optionally, include an antioxidant, a chelating agent, or both. While not desiring to be bound to any particular theory, the antioxidant may assist in stabilizing the formulation film by assisting in reducing, and preferably eliminating, any color change therein during the shelf life of the formulation film and/or system incorporating the film, and/or oxidation and associated degradation of fenretinide, while the chelating agent may bind, or form a complex with, any trace metals that may be present in the ingredients present in the formulation or formulation film, thereby reducing, and desirably precluding, any ability of these metals to catalyze oxidation reactions.

Antioxidants that may be used in aspects of the present invention include, without limitation, alpha tocopherol, ascorbic acid, ascorbyl palmitate, butylated hydroxyanisole (BHA), butylated hydroxytoluene (BHT), monothioglycerol, potassium metabisulfite, propionic acid, propyl gallate, sodium ascorbate, sodium bisulfite, sodium metabisulfite, and sodium sulfite, with butylated hydroxytoluene and ascorbyl palmitate being preferred. Chelating agents that may be used in aspects of the present invention include, without limitation, ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof.

If included, an antioxidant and chelating agent may each be present (alone or together) in an amount ranging from about 0.01 wt. % to about 2 wt. %, and more desirably from about 0.02 wt. % to about 1 wt. %, and even more desirably from about 0.04 wt. % to about 0.6 wt. %.

In a further aspect, the present invention provides a formulation comprising, consisting essentially of, or consisting of, fenretinide, povidone, a solubilizer, and HPC. Solubilizers may perform one or more of several functions in the inventive formulations, including, without limitation, assisting in the solubilization of the API in the formulation and its release from the inventive formulation. In certain aspects, the solubilizer comprises, consist essentially of, or consists of one or more of a nonionic surfactant, e.g., polysorbate 80 (Tween® 80), a bile acid salt (e.g., sodium deoxycholate, a detergent which solubilizes fats), dimethyl sulfoxide (DMSO), tetraethylene glycol, dipropylene glycol, polyethylene glycol, and mixtures thereof. Desirably, aspects of the invention comprise a solubilizer that is a nonionic surfactant, and even more desirably polysorbate 80. Preferably, the formulation aspects of the invention include limited amounts of a bile acid salt (e.g., sodium deoxycholate, a detergent which solubilizes fats), dimethyl sulfoxide (DMSO), tetraethylene glycol, dipropylene glycol and polyethylene glycol. If present, these excipients desirably are limited to an amount ranging from about 0.001 wt. % to about 2, 1, 0.5, or 0.01 wt. % and, more preferably, the formulations have no detectable amount of these excipients.

In aspects of the invention wherein a solubilizer and permeation enhancer are included in the inventive formulations, it was discovered that the amount of solubilizer in such formulations should be limited to no more than about 5 wt. %, as solubilizer in excess of this amount was unexpectedly found to be unnecessary to provide the desired properties of the inventive formulation. In this regard, and if present, the solubilizer may be included in the inventive formulations at from about 0.1, 0.5 or 1 wt. % to about 2, 3, 4 or 5 wt. %, and more desirably from about 0.5 wt. % to about 5 wt. %, and even more desirably from about 1 wt. % to about 3 wt. %.

In aspects of the invention which include a solubilizer but not a permeation enhancer in the inventive formulations, the amount of solubilizer may be increased relative to the amount used when permeation enhancers are included. For example, the solubilizer may be included in such formulations in an amount of 1, 2, 3, 4, 5, 6, 7, 8, 9 or 10 wt. % up to about 12, 13, 14 or 15 wt. %, desirably about 3 to about 15 wt. %, and more desirably about 5 wt. % to about 12 wt. %.

Another aspect of the invention provides formulations comprising, consisting essentially of, or consisting of, fenretinide, a permeation enhancer, povidone, and HPC.

A further aspect of the invention provides formulations comprising, consisting essentially of, or consisting of, fenretinide, a permeation enhancer, a solubilizer, and HPC.

In yet another aspect, the present invention provides formulations comprising, consisting essentially of, or consisting of, fenretinide, a permeation enhancer, a solubilizer, povidone, and HPC.

Another aspect of the invention provides a formulation comprising, consisting essentially of, or consisting of, fenretinide, a plasticizer, povidone, and HPC, as well as, optionally, a solubilizer and/or a permeation enhancer. A plasticizer may perform one or more of several functions in the inventive formulations, including, without limitation, assisting in providing flexibility to the formulation film and dosage forms prepared therefrom. In aspects of the invention wherein a plasticizer is included in the formulations, the plasticizer may desirably comprise an ester of citric acid or salt thereof, such as, for example, triethylcitrate and/or triethyl-2-acetylcitrate, and more desirably both such citrates.

In aspects of the invention wherein a plasticizer is included in the inventive formulations, it was discovered that the amount of plasticizer in such formulations may be included in the inventive formulations at from about 5, 10, 15, 16, 17, 18 19 or 20 wt. % up to about 25, 26, 27, 28 29 or 30 wt. %, desirably from about 15 to about 25 wt. %, more desirably from about 20 to about 25 wt. %, and most desirably about 20 wt. %.

The plasticizer desirably comprises, consists essentially of, or consists of triethylcitrate and/or triethyl-2-acetylcitrate, but more desirably both are present. When both are present in the formulation, triethyl-2-acetylcitrate may desirably be present in an amount ranging from about 1, 5, 6, 7, 8, 9 or 10 wt. % up to about 20, 21, 22, 23, 24 or 25 wt. %, desirably from about 5 wt. % to about 20 wt. %, more desirably from about 10 wt. % to about 20 wt. %, and most desirably about 15 wt. %, while triethylcitrate desirably may be present in an amount ranging from about 1, 2, 3 or 4 wt. % to about 7, 8, 9, 10, 11, 12, 13, 14 or 15 wt. %, more desirably from about 2 wt. % to about 10 wt. %, even more desirably from about 3 wt. % to about 8 wt. %, and most desirably about 5 wt. %.

In related aspects of the invention wherein the plasticizer comprises, consists essentially of, or consists of, triethylcitrate and triethyl-2-acetylcitrate, the weight ratio of triethyl-2-acetylcitrate to triethylcitrate may range from about 1:1 to about 3:1, desirably from about 2:1 to about 3:1, and most desirably about 3:1.

Additional aspects of the present invention contemplate the plasticizers being included therein in both the aforedescribed weight ratios and weight percentages.

In another aspect, the present invention provides a formulation comprising fenretinide, a solubilizer, povidone, a plasticizer, and HPC, while a related aspect further includes a permeation enhancer.

In a further aspect, the invention provides a formulation comprising, consisting essentially of, or consisting of, (a) fenretinide, (b) propylene glycol (PG), a terpene, a terpenoid, and mixtures thereof, and (c) HPC.

Another aspect of the invention provides a formulation comprising, consisting essentially of, or consisting of, fenretinide, PG, menthol, and HPC.

A further aspect of the present invention provides a formulation comprising fenretinide, PG, menthol, a citrate ester, and HPC.

Additional aspects of the invention provide a formulation comprising fenretinide, povidone, a citrate ester, and HPC, while in related aspects there is further included therein a surfactant, desirably a nonionic surfactant.

Other aspects of the present invention provide a formulation comprising fenretinide, PG, menthol, povidone, a citrate ester, and HPC, while in related aspects there is further included therein a solubilizer, desirably a nonionic surfactant.

It is contemplated, and should be understood, that each of the aforedescribed aspects of the inventive formulations may include what is referred to as the desirable or preferred aspects of the invention as described herein, e.g., the desirable or preferred specific permeation enhancers, plasticizers, solubilizers and HPC grades, the desirable or preferred amounts of these and other general and specific ingredients, and combinations of the desired or preferred specific ingredients and amounts thereof as described herein.

Other aspects of the invention contemplate including the inventive formulations described herein in a mucoadhesive delivery system. Such systems comprise, consist essentially of, or consist of, an inventive formulation film per se as described herein, but optionally (and desirably) also include a backing layer attached to the formulation film (which, when a backing is present, may be referred to as a patch) that delivers the fenretinide transmucosally from the formulation film to provide for the treatment of a precancerous lesion in the stratified squamous epithelium.

These systems, which may also be referred to as dosage forms, may be provided in any shape or size (e.g., formulation surface area), and desirably in a variety of sizes sufficient to enable treatment of various-sized precancerous lesions (e.g., to cover the entire surface area of the lesion), whether via the application of a single or multiple dosage forms. The shapes of the systems may be circular, oval, ellipsoidal or an irregular shape, but desirably exclude sharp (non-rounded) corners to minimize patient irritation during use. The formulation film used in the systems may desirably range in area from about 3 cm² to about 12 cm², and more desirably from about 5 cm² to about 10 cm². The thickness of the system (e.g., patch) is also desirably limited to maximize patient comfort, and may be desirably between about 0.05 mm to about 0.5 mm.

Figure 1B:
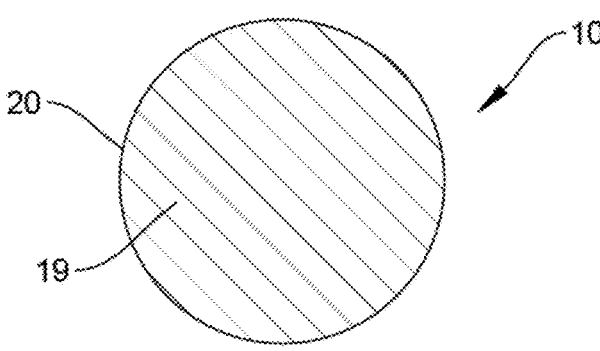
Figure 1C:
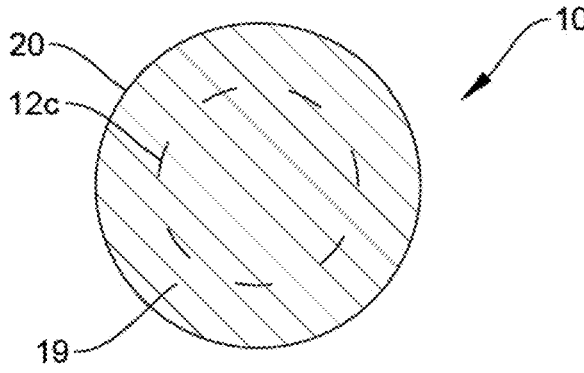
Figure 2A:
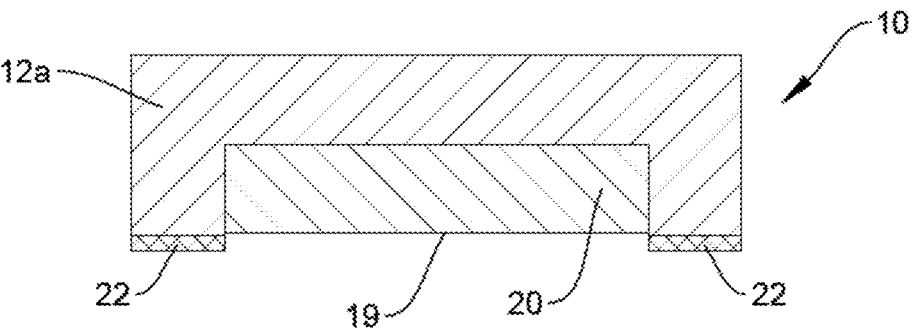
Figure 2B:
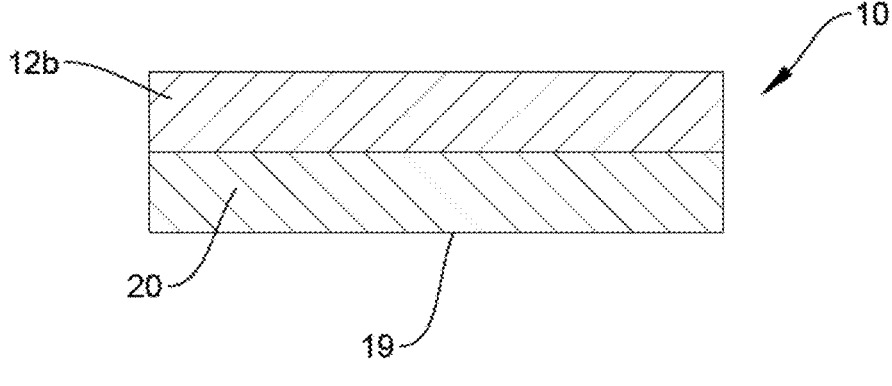
Figure 2C:
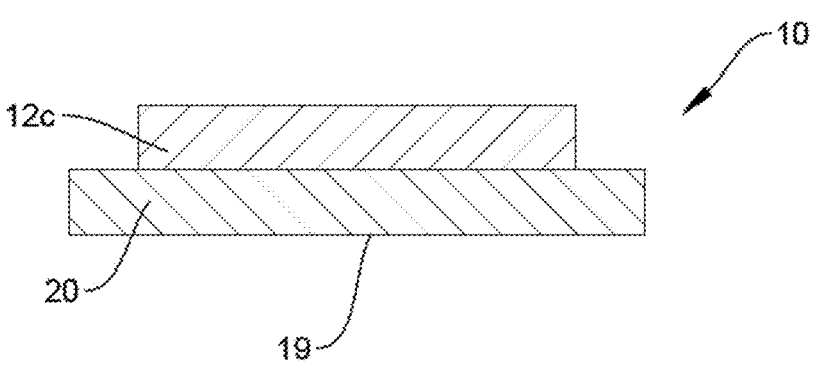

Turning to FIGS. 1A to 1C, there are illustrated aspects of the present invention constituting variations of individual dosage forms 10 in the form of a circular patch. FIGS. 2A-2C are cross-sectional views of FIGS. 1A to 1C, respectively. Each of these dosage forms includes an inventive fenretinide-containing formulation (as described herein) in the form of a relatively thin film 20, and a backing layer of differing areas (12a, 12b and 12c in FIGS. 2A, 2B and 2C, and 12a and 12c in FIGS. 1A and 1C, the backing layer being present but not visible in FIG. 1B). The backing layer is water-insoluble, and functions as a barrier to prevent the fenretinide from being released therethrough. The backing layer may vary in area, and may extend beyond the periphery of the formulation film 20 (as illustrated in FIGS. 1A and 2A), be coextensive with the periphery of the film 12b (as illustrated in FIGS. 1B and 2B), or the periphery of the film may extend beyond the periphery of the backing layer 12c (as illustrated FIGS. 1C and 2C). The fenretinide-containing film has an outer surface 19 that is exposed when a cover sheet (not shown) is removed prior to application of the outer surface onto a precancerous lesion. When applied onto a patient, the fenretinide-containing film will adhere to the mucosa, and release fenretinide into the precancerous lesion. When additional adhesion to the mucosa is desired, any portion of the backing layer extending beyond the periphery of the formulation film (e.g., 12a in FIGS. 1A and 1B) may have a mucoadhesive 22 applied thereon.

The preparation of the inventive formulations used to provide a film for use in the systems and therapeutic methods described herein is as follows. Fenretinide and any permeation enhancers (e.g., menthol, propylene glycol) are dissolved (with mixing) in a polar organic solvent (desirably a combination of two or more of acetone, ethanol, or isopropanol, and more desirably ethanol and isopropanol in equal proportions) to form a solution. The amount of polar solvent used in the preparation may vary, and should be sufficient to provide a finished solution of the formulation that can be cast onto a release sheet and dried to provide a formulation film. This amount is typically about 70 to about 90 wt. %, desirably about 75 to about 85 wt. %, and more desirably about 80 wt. %, relative to the total weight of the other formulation ingredients. Thereafter, the cellulosic polymer and, if desired, plasticizers, and any other excipients, are added to the fenretinide solution and, with mixing, form a viscous solution. Any desired solubilizer is then added thereto, with mixing, to form a finished solution.

The preparation of the formulation film may be undertaken by casting the finished viscous solution onto a polymeric or paper support layer at a thickness of about 1.5 to about 1.7 mm, and then dried in a convection oven (e.g., 70° C. for about 30 minutes), to form a thin film (about 0.1 to about 0.2 mm in thickness). If desired, a separate liquid polymeric composition, serving as the backing layer for the API-containing formulation film, may be applied onto to the formulation film. This backing layer composition may comprise an acrylate/methacrylate polymer, a volatile carrier, and, if desired, a colorant (e.g., TiO₂). After this composition is applied onto one side of a formulation film, the backing layer composition may be dried at 75° C. for 30 minutes to provide a bilayer structure that may be converted into a plurality of individual dosage forms, e.g., patches, via any suitable means, such as die cutting.

Alternatively, the viscous API-containing formulation solution may be coated onto the pre-dried protective backing layer, and subsequently dried in a convection oven to form a bilayer structure.

A release layer may be applied onto one side of the formulation film if a backing layer is present, or onto both sides of the film if a backing layer is not present, which release layer is removed prior to application of the film onto the precancerous lesion.

In related aspects, the invention provides methods for the treatment of a patient afflicted with precancerous lesions in the stratified squamous epithelium of mucosal tissue, and desirably mucosal tissue in the oral cavity (constituting the lips, the inside lining of the lips and cheeks (as referred to as the buccal mucosa), the teeth, the front two-thirds of the tongue, the floor of the mouth beneath the tongue, the hard palate and the retromolar region), the oropharynx (constituting the middle part of the throat, including the base of the tongue (back third), the soft palate, the tonsils and the side and back walls of the throat).

In each of the inventive methods for treatment of a patient afflicted with precancerous lesions in the stratified squamous epithelium, the methods comprise, consist essentially of, or consist of, applying an inventive formulation film (alone or as part of a system) onto a precancerous lesion in the stratified squamous epithelium of a patient, and releasing fenretinide from the formulation film onto the lesion.

When a system is used in the inventive methods, the formulation film thereof is applied against the lesion by the healthcare provider or patient, with the backing layer being used by the provider or patient to apply sufficient pressure, for a sufficient period of time, to enable adhesion of the system onto the mucosa in a manner that enables the formulation film to release fenretinide onto the lesion.

Desirably, the method further contemplates that the formulation resides on the lesion for a time sufficient to deliver a therapeutic dose of fenretinide to the lesion. A therapeutic dose of fenretinide is one that, for a particular precancerous lesion: (a) causes regression of the lesion, (b) modulates the progression of the lesion into carcinoma, or (c) prevents the progression of the lesion into carcinoma. Such therapeutic doses of fenretinide may range from about 0.1 to about 10 μM in the mucosal tissue undergoing therapy.

The precise residence time for the inventive formulation film on a lesion may vary depending, primarily, on the API-loading of the formulation (higher concentration of API providing a greater quantity, and faster, release of API from the formulation relative to a lower API concentration), the adhesivity of the formulation onto the tissue (relatively greater adhering formulation providing a greater release of API relative to a poorly adhering formulation), and the topography of the lesion (release of a greater quantity of API generally corresponding with greater area of contact), but may commonly vary between 1 and 60 mins, and more commonly between 15 and 30 minutes. As the therapy is typically performed by a healthcare provider, a more limited residence time is preferred, particularly for patient comfort and compliance.

Application of the formulation onto a lesion may be repeated, for example, daily, or twice daily, for at least 1, 2, 3, 4, 6, 8, 10 or 12 weeks, or more desirably for a period of time until the desired therapeutic benefit is achieved. A healthcare provider should be able to assess (visually) whether the therapy has had an effect on the precancerous lesion within 30 days after therapy is concluded. However, it should be understood that, in many cases, precancerous oral lesions cannot be fully eradicated, and thus a patient is often required to undergo therapy in perpetuity to decrease the likelihood that a precancerous lesion will progress to SCC.

Unexpected advantages associated with the various aspects of the present invention include providing fenretinide-containing formulations and related systems that exhibit desirable physical attributes while also providing transmucosal therapy to patients afflicted with precancerous lesions in stratified squamous epithelium.

As one example of the desirable physical attributes, the conversion of relatively large sheets (film) of the inventive formulation into relatively smaller individual dosage forms may be provided using mechanical means (e.g., die cutting)

without inflicting physical damage (e.g., shattering, cracking, splitting or chipping) to the relatively large sheet or the individual dosage forms. In addition, the formulation, and specifically individual dosage forms (which may be in the form of patches), are sufficiently flexible to permit pre-application handling by a healthcare provider or patient, as well as application of the dosage form onto precancerous lesions in the stratified squamous epithelium of a patient, without the infliction of similar types of physical damage to the dosage form.

Desirably, the fenretinide-containing formulations and related systems of the present invention exhibit the aforesaid physical attributes and one, more than one, and preferably all, of the following: relatively high loading of fenretinide; release of desired amounts of fenretinide from the formulation film within a desired time period; delivery of therapeutic amounts of fenretinide into the desired situs, e.g., precancerous lesions on stratified squamous epithelium; good mucoadhesive properties; and a relatively smooth, non-irritating, contacting surface.

The inventive formulations, systems and methods provide the further advantage of local distribution of the fenretinide to treat the precancerous lesion in stratified squamous epithelium, precluding undesirable systemic levels of fenretinide in the blood.

Tables A, B, C and D provide a series of illustrative fenretinide-containing formulations in accordance with the present invention.

TABLE A

| Ingredient | Formulation 1 (wt. %) | Formulation 2 (wt. %) | Formulation 3 (wt. %) | Formulation 4 (wt. %) |
|---|---|---|---|---|
| Fenretinide | 0.1-20 | 5-20 | 10-15 | 15 |
| Propylene Glycol (PG) | 1-15 | 5-10 | 6-9 | 7 |
| Menthol | 5-25 | 10-20 | 12-18 | 15 |
| Polyvinyl Pyrrolidone (PVP) | 1-30 | 15-30 | 20-25 | 20 |
| Hydroxypropylcellulose (HPC) | 1-40 | 5-30 | 15-25 | 20-25 |

TABLE B

| Ingredient | Formulation 1 (wt. %) | Formulation 2 (wt. %) | Formulation 3 (wt. %) | Formulation 4 (wt. %) |
|---|---|---|---|---|
| Fenretinide | 0.1-20 | 5-20 | 10-15 | 15 |
| Propylene Glycol (PG) | 1-15 | 5-10 | 6-9 | 7 |
| Menthol | 5-25 | 10-20 | 12-18 | 15 |
| Polyvinyl Pyrrolidone (PVP) | 1-30 | 15-30 | 20-25 | 20 |
| Triethylcitrate and/or triethyl-2-acetylcitrate | 10-30 | 15-25 | 20-25 | 20 |
| Hydroxypropylcellulose (HPC) | 1-40 | 5-30 | 15-25 | 20-25 |
| Solubilizer | 0.1-5 | 0.5-4 | 1-3 | 2 |

TABLE C

| Ingredient | Formulation 1 (wt. %) | Formulation 2 (wt. %) | Formulation 3 (wt. %) | Formulation 4 (wt. %) |
|---|---|---|---|---|
| Fenretinide | 0.1-20 | 5-20 | 10-15 | 15 |
| Propylene Glycol (PG) | 1-15 | 5-10 | 6-9 | 7 |
| Menthol | 5-25 | 10-20 | 12-18 | 15 |
| Polyvinyl Pyrrolidone (PVP) | 1-30 | 15-30 | 20-25 | 20 |
| Triethylcitrate | 1-15 | 2-10 | 3-8 | 5 |
| Triethyl-2-acetylcitrate | 1-25 | 5-20 | 10-20 | 15 |

TABLE C-continued

| Ingredient | Formulation 1 (wt. %) | Formulation 2 (wt. %) | Formulation 3 (wt. %) | Formulation 4 (wt. %) |
|---|---|---|---|---|
| Hydroxypropylcellulose (HPC) | 1-40 | 5-30 | 15-25 | 20-25 |
| Solubilizer | 0.1-5 | 0.5-4 | 1-3 | 2 |

TABLE D

| Ingredient | Formulation 1 (wt. %) | Formulation 2 (wt. %) | Formulation 3 (wt. %) |
|---|---|---|---|
| Fenretinide | 10-20 | 14-16 | 15 |
| Propylene Glycol (PG) | 6-9 | 7-8 | 7.5 |
| Menthol | 12-18 | 14-16 | 15 |
| Polyvinyl Pyrrolidone - PVP (Plasdone ™ K29/32) | 8-12 | 9-11 | 10 |
| Polyvinyl Pyrrolidone - PVP (Plasdone ™ K90) | 8-12 | 9-11 | 10 |
| Triethylcitrate | 4-6 | 4-6 | 5 |
| Triethyl-2-acetylcitrate | 12-18 | 14-16 | 14.95 |
| Hydroxypropylcellulose - HPC (Klucel ™ JF) | 8-12 | 9-11 | 10 |
| Hydroxypropylcellulose - HPC (Klucel ™ GF) | 8-12 | 9-11 | 10 |
| Polysorbate 80 | 1-5 | 2-3 | 2.5 |
| Preservative (BHT) (optional) | 0.001-0.1 | 0.03-0.07 | 0.05 |

It should be appreciated that, consistent with the description herein, the inventive formulations described in Tables A-D desirably do not contain: (a) cellulose-based excipients that are sparingly, or insoluble, in water, such as microcrystalline cellulose (MCC) and ethyl-containing celluloses (e.g., ethyl cellulose (EC), hydroxyethyl cellulose (HEC)), nor cellulose-based excipients that exhibit very limited solubility in polar organic solvents, such as, for example, methyl-containing celluloses (e.g., hydroxypropyl methyl-cellulose (HPMC), carboxymethylcellulose (CMC), meth-ylcellulose (MC)) and/or (b) polymers and/or copolymers of acrylic acid, acrylate and/or esters thereof. It should be further understood that for each numerical range provided in these tables, the numerals associated with each range may be preceded by the term "about," e.g., 14-16 includes "about 14-about 16"; 7.5 includes "about 7.5".

The inventive fenretinide-containing formulations may provide desirable transmucosal drug release rates, as well as desirable flux values, and more desirably both such rates and values. Drug release rates of the fenretinide-containing formulation films may range from at least about 30, 35 or 40% to about 45, 50, 55 or 60% of fenretinide contained in a formulation film over 60 mins, and/or at least about 70, 75, 80, 85 or 90% and up to about 92, 95, 97 or 99% of fenretinide contained in a formulation film over 60 mins, as determined by the methodology described in the following paragraph.

The drug release rates provided by aspects of the present invention were assessed by placing a formulation film in a USP dissolution apparatus (900 mL of dissolution media (80% isopropyl alcohol+20% of 1.0% sodium dodecyl sulfate (SDS) in water at 37° C.). A paddle over disk was used to retain the formulation film sample. The apparatus was operated at 100 rpm, with samples being taken at 15, 30, 45, 60 and 75 mins and assayed for fenretinide concentration via HPLC.

Flux values of the inventive fenretinide-containing formulation films may range from at least about 0.1 and up to about 2 $\mu g/cm^2/hr$, over six hours, as determined by the following methodology. Frozen, posterior torso, split-thickness human cadaver skin was received and utilized upon thawing. Tissue samples were cut to size for mounting onto upright Franz diffusion cells and allowed to equilibrate for one hour at room temperature, with the dermis side of each skin sample contacting temperature-controlled (32.5° C.) 1% Tween receiver media during that one hour period. After the expiration of this one hour period, 25 $\mu L$ DPBS (Dulbecco's phosphate-buffered saline) was pipetted onto the center of each tissue sample, followed by application of one 1.039 $cm^2$ unit of inventive formulation film onto the wetted tissue surface, followed by pipetting 25 $\mu L$ DPBS onto the top surface of the formulation film. The Franz cell then was capped with a donor cover and the Franz cells were brought to 8.0 mL volume with fresh receiver media. For each specified sampling time, the media was removed from each Franz cell and replaced with a fresh volume of receiver media until the next specified sampling time. This experimental sequence was repeated for all time points at 0.5, 1.0, 2.0, 4.0, and 6.0 hours. The receiver media from each cell was transferred to HPLC vials and analyzed via UPLC/UV.

At specified times (30 mins and 6 hours), cadaver tissue was removed from the Franz cell, wiped dry with a Kimwipe to remove any residual formulation, with the tissue then being placed into a 1.5 mL centrifuge tube. The tissues were then extracted in DMSO and ethanol to recover the fenretinide in the tissue, with the extracted liquid being analyzed to determine the amount of fenretinide therein (and, thus, assess the amount of fenretinide that had passed from the formulation film into the tissue at the particular time point).

EXAMPLES

The present invention is further illustrated by the following examples. These examples, while providing, in part, details on preferred embodiments of the invention, are illustrative and should not be construed as limiting the scope of the invention.

Preparation of the Formulation Samples

Fenretinide, menthol, propylene glycol, triethyl citrate, triethyl-2-acetyl citrate, and Plasdone™ K29/32 were added to a 1:1 mixture of isopropanol and ethanol and mixed on a jar roller until dissolved, forming a transparent, yellow solution. Plasdone™ K90 was weighed separately and added to this solution, and the contents were mixed on a jar roller to facilitate dissolution of the Plasdone™ K90. A transparent, yellow, viscous solution was formed. Klucel™ JF and Klucel™ GF were weighed separately and added to this viscous solution, and the contents were mixed to facilitate dissolution of the HPC polymers. A transparent, yellow, viscous gel was formed. Tween® 80 was then added to the formulation and mixed until the Tween® 80 was uniformly distributed throughout the viscous composition, while avoiding significant bubble formation.

The resulting viscous composition was then applied onto a casting release liner support (silicone-coated polyester film or paper) to a thickness of about 1.5 to about 1.7 mm, and then dried 70° C. for 30 minutes. The resulting formulation film was removed from the casting release liner support and subjected to testing.

Example 1

This example provides an assessment of the mucoadhesive properties and flexibility of a variety of fenretinide-containing films.
A. Mucoadhesion Analysis To assess the mucoadhesion of a formulation, the general approach was to quantify the force required to remove each formulation film from a glass plate that was pre-wetted with artificial saliva. The higher the removal force, the greater the mucoadhesion.

Each formulation film sample to be tested was obtained from a sheet of a formulation film prepared in the manner described in the preceding section entitled "Preparation of the Formulation Samples," with each sample comprising a thin circular disc having a surface area of 52 mm².

The artificial saliva was prepared as follows. 200 mL of HPLC grade water was introduced into a flask. A stir bar was then introduced into the flask to provide mixing during the preparation. The following salts were then added individually into the water-filled flask, allowing each salt to dissolve (dissolution being determined via visual observation, about 15 mins of magnetic stirrer mixing at a setting 6-7) before adding the next salt: 0.409 g potassium phosphate monobasic; 0.585 g sodium chloride; and 0.056 g calcium chloride dihydrate or 0.042 g calcium chloride anhydrous. After all salts are completely dissolved and while the solution is mixing, the pH of the solution was adjusted to 6.2 to 6.6 (at room temperature) by adding 1N sodium hydroxide solution as necessary in a dropwise manner. Thereafter, the solution was transferred to a 250 mL flask, filled with HPLC grade water until the final volume was 250 mL, and thoroughly mixed by inverting the flask about six times to provide the finished artificial saliva solution. The artificial saliva was stored at room temperature (or refrigerated 2° C. to 8° C.) and used within 14 days of its preparation.

The device used to assess the removal force was a TA.XT.plus Texture Analyzer with Exponent [Connect] software (v. 6.1.16.0) (Stable Micro Systems, Surrey, United Kingdom) being used to provide for data collection and analysis. The Texture Analyzer was set to the following parameters: pre-test speed: 0.1 mm/sec; test speed: 0.01 mm/sec; post-test speed: 0.1 mm/sec; applied force: 100 g; return distance: 4 mm; contact time: 5 sec (i.e., the time the formulation sample is in contact with the artificial saliva/glass plate); trigger type: auto; trigger force: 1 g; tare mode: auto; delay acquisition: off; advanced options: on; proportional gain: 50; integral gain: 20; differential gain: 5 and max. tracking speed: 5 mm/sec. Thereafter, the calibrate force, check force and calibrate height was executed with the probe and glass plate secured in place.

The sample preparation began by affixing the liner side of a formulation film sample onto the underside of a flat probe (No. TA-10SS, a cylindrical one-half inch stainless steel probe) using double-sided tape, without any of the tape extending beyond the outer perimeter of the sample. The adhesive on the tape should be of a strength so that the values obtained will represent the mucoadhesive properties of the side of the formulation sample not in contact with the tape. The probe, with the sample affixed thereto, was then attached to the Texture Analyzer. A TA-90 heavy duty platform with HDP/90-PG7 (circular glass plate) was positioned on the base of the Texture Analyzer directly below the probe. 50 μL of artificial saliva was then applied onto the glass plate as a single droplet centered under the probe. During testing, the saliva was at room temperature, free of crystals and other visually observable contamination, and had a pH of 6.2 to 6.6. The testing was then commenced, with the maximum (peak) force required for removal of the formulation sample from the artificial saliva-containing glass plate (after a dwell or contact time of 5 seconds), as well as the area under the curve wherein the curve is defined by a plot of force (grams) v. time (sec), being measured and recorded. The average of the maximum force (in grams) and area under the curve obtained from testing three samples of the same formulation, is reported for each formulation in Tables 1.1 and 1.2 as "Ave. Force (g)" and "Ave. Area (g*s)," respectively.
B. Flexibility Analysis To assess the flexibility of a formulation film, the following procedure was used. Each formulation film sample that was tested was obtained from a sheet of formulation film prepared in the manner described in the preceding section entitled "Preparation of the Formulation Samples," and comprised a thin (approximately 127 microns) 6 inch×8 inch film sheet. The sheet was folded over onto itself (the 6-inch sheet edges were brought together) and a visual observation was made to assess whether or not the sheet developed a crack while folding. If the film cracked during folding, it was categorized as "brittle"; a film that did not crack during folding was categorized as "flexible."
C. Assessment of Film Properties It was discovered that fenretinide-containing films disclosed in U.S. Pat. No. 10,758,619 (the "'619 patent) and Desai et al., "Development and In Vitro-In Vivo Evaluation of Fenretinide-Loaded Oral Mucoadhesive Patches for Site-Specific Chemoprevention of Oral Cancer," *Pharm. Res.* 20:2599-2609 (2011) ("Desai") were relatively fragile, adversely affecting their efficient manufacturing of individual dosage forms and/or clinical use, e.g., the handling and placement of the formulation film by a healthcare provider onto a precancerous lesion in the squamous epithelial tissue of a patient.

Examples 1-13 in Tables 1.1 and 1.2 represent mucoadhesive fenretinide formulation films based on excipients disclosed in the '619 patent and/or Desai, wherein the present inventors attempted to develop a fenretinide formulation film which possessed reduced brittleness without unduly sacrificing mucoadhesion.

Examples 14-23 in Tables 1.1 and 1.2 represent fenretinide mucoadhesive formulation films that exhibited enhanced flexibility relative to the films of Examples 1-13 as well as desirable mucoadhesion (average force and average area under the curve) as measured by the protocol described herein.

TABLE 1.1

| Example | Fenretinide | PG | Menthol | K29/32 | K90 | JF | TR-1 | AA-1 | GF | TEAC | TEC |
|---|---|---|---|---|---|---|---|---|---|---|---|
| 1 | 5.0 | 1.4 | 2.8 | — | — | — | — | — | — | — | — |
| 2 | 9.5 | 3.9 | 7.9 | 70.9 | — | — | — | — | — | — | — |
| 3 | 8.0 | 3.3 | 6.7 | 60.1 | — | — | — | — | — | — | — |
| 4 | 8.8 | 3.6 | 7.3 | 65.6 | — | — | — | — | — | 7.4 | — |
| 5 | 9.3 | 3.9 | 7.7 | 69.8 | — | — | 0.4 | 1.2 | — | — | — |
| 6 | 7.4 | 3.1 | 6.1 | 55.5 | — | — | 1.0 | 0.3 | — | 6.3 | — |
| 7 | — | 2.7 | 5.3 | 61.0 | — | — | 0.5 | 1.6 | — | 7.9 | — |
| 8 | — | 2.5 | 5.0 | 55.4 | — | — | 0.5 | 1.5 | — | 15.0 | — |
| 9 | 5.0 | 2.5 | 5.0 | 60.0 | — | — | — | — | — | 7.5 | — |
| 10 | 5.9 | 2.9 | 5.9 | 70.6 | — | — | — | — | — | 8.8 | — |
| 11 | — | 2.5 | 5.0 | 57.5 | — | — | — | — | — | 10.0 | 10.0 |
| 12 | — | 2.5 | 5.0 | 28.7 | 28.7 | — | — | — | — | 9.9 | 10.3 |
| 13 | 4.9 | 4.0 | 4.8 | 27.0 | 27.1 | — | — | — | — | 10.9 | 9.7 |
| 14 | 15.0 | 7.4 | 15.1 | 10.2 | 10.2 | 10.2 | — | — | 10.3 | 10.0 | 10.2 |
| 15 | 14.9 | 7.6 | 15.0 | 10.6 | 11.0 | 10.5 | — | — | 10.6 | 10.0 | 9.9 |
| 16 | 14.9 | 7.6 | 15.0 | 10.6 | 11.0 | 10.5 | — | — | 10.6 | 10.0 | 9.9 |
| 17 | — | 8.9 | 17.6 | 12.2 | 12.2 | 12.2 | 1.2 | — | 12.2 | 11.8 | 11.7 |
| 18 | — | 8.9 | 17.6 | 12.2 | 12.2 | 12.2 | 1.2 | — | 12.2 | 11.8 | 11.7 |
| 19 | 14.9 | 7.5 | 14.9 | 12.7 | 12.7 | 12.7 | — | — | 12.7 | — | 10.2 |
| 20 | 14.9 | 7.7 | 14.9 | 12.7 | 12.7 | 12.7 | — | — | 12.7 | 10.0 | — |
| 21 | 15.0 | 7.4 | 15.1 | 10.2 | 10.2 | 10.2 | — | — | 10.3 | 10.0 | 10.2 |
| 22 | 15.0 | 7.5 | 15.0 | 10.0 | 10.0 | 10.0 | — | — | 10.0 | 15.1 | 5.1 |
| 23 | 15.1 | 7.5 | 15.0 | 10.2 | 10.2 | 10.3 | — | — | 10.2 | 10.0 | 10.0 |

TABLE 1.2

| Example | Tween 80 | SD | RL-PO | EPO | NM30D | Contact Time | Average Force (g) | Average Area (g*s) | Flexibility |
|---|---|---|---|---|---|---|---|---|---|
| 1 | 11.3 | 22.7 | 56.8 | — | — | 5 | 102.1493 | 11.83367 | Brittle |
| 2 | — | — | 7.9 | — | — | 5 | 240.0567 | 62.78233 | Brittle |
| 3 | 15.2 | — | 6.7 | — | — | 5 | 467.9707 | 254.041 | Brittle |
| 4 | — | — | 7.3 | — | — | 5 | 607.8333 | 403.7107 | Brittle |
| 5 | — | — | 7.7 | — | — | 5 | 178.5707 | 107.1687 | Brittle |
| 6 | 14.1 | — | 6.1 | — | — | 5 | 363.0037 | 207.3553 | Brittle |
| 7 | 15.8 | — | 5.3 | — | — | 5 | 466.797 | 274.961 | Brittle |
| 8 | 15.0 | — | 5.0 | — | — | 5 | 403.3093 | 249.5717 | Brittle |
| 9 | 15.0 | — | — | 5.0 | — | 5 | 434.728 | 270.7317 | Brittle |
| 10 | — | — | — | 5.9 | — | 5 | 640.2853 | 490.2613 | Brittle |
| 11 | 10.0 | — | — | 5.0 | — | 5 | 483.6327 | 275.4987 | Brittle |
| 12 | 10.0 | — | — | 5.0 | — | 5 | 508.8997 | 281.0787 | Brittle |
| 13 | 6.3 | — | — | — | 5.4 | 5 | 383.6177 | 161.6417 | Brittle |
| 14 | 1.5 | — | — | — | — | 5 | 496.3463 | 197.036 | Flexible |
| 15 | — | — | — | — | — | 5 | 423.667 | 156.552 | Flexible |
| 16 | — | — | — | — | — | 5 | 239.3968 | 64.4925 | Flexible |
| 17 | — | — | — | — | — | 5 | 453.6943 | 172.4215 | Flexible; oily surface phase |
| 18 | — | — | — | — | — | 5 | 428.1177 | 158.293 | Flexible; oily surface phase |
| 19 | 1.7 | — | — | — | — | 5 | 215.5803 | 52.9895 | Flexible |
| 20 | 1.8 | — | — | — | — | 5 | 341.1398 | 104.1485 | Flexible |
| 21 | 1.5 | — | — | — | — | 5 | 244.1473 | 54.73733 | Flexible |
| 22 | 2.5 | — | — | — | — | 5 | 424.9347 | 139.159 | Flexible |
| 23 | 1.5 | — | — | — | — | 5 | 216.5167 | 48.51633 | Flexible |

The ingredients in Tables 1.1 and 1.2 (and as may be further described elsewhere) are as follows:

Fenretinide: N-(4-hydroxyphenyl) retinamide (Olon S.p.A., Milan, IT)

Menthol: USP grade (EMD Chemicals, Gibbstown, NJ)

PG: propylene glycol, USP grade (Spectrum Chemical, New Brunswick, NJ)

K29/32: Plasdone™ K29/32, water-soluble polyvinyl pyrrolidone (linear homopolymer of n-vinyl-2-pyrrolidone (Ashland Inc., Kentucky, US); weight average Mw of about 58,000 Daltons K90: Plasdone™ K90, water-soluble polyvinyl pyrrolidone (linear homopolymer of n-vinyl-2-pyrrolidone (Ashland Inc., Kentucky, US); weight average Mw of about 1,300,000 Daltons JF: Klucel™ hydroxypropylcellulose (HPC) JF Grade (Ashland Inc., Kentucky, US); Mw of about 140,000 Daltons TR-1: Permulen TR-1, a high molecular weight, (non-ethoxylated) crosslinked copolymer of acrylic acid and a hydrophobic $C_{10-30}$ alkyl acrylate co-monomer, NF grade (Lubrizol Advanced Materials, Wickliffe, OH, US).

AA-1: Noveon AA-1, a high molecular weight acrylic acid polymer crosslinked with divinyl glycol, USP grade (Lubrizol Advanced Materials, Wickliffe, OH, US)

GF: Klucel™ hydroxypropylcellulose (HPC) GF Grade (Ashland Inc., Kentucky, US); Mw of about 370,000 Daltons TEAC: triethyl-2-acetylcitrate, NF grade (Vertellus LLC, Indiana, US)

TEC: triethylcitrate, NF grade (Vertellus LLC, Indiana, US)

Tween® 80: a nonionic surfactant, more specifically a polyethylene sorbitol ester (aka polyoxyethylene sorbitan monooleate), NF grade (Merck, KGaA)

SD: sodium deoxycholate: the sodium salt of a bile acid, deoxycholic acid (SAFC, Millipore-Sigma, Milwaukee, MN)

RL-PO: Eudragit® RL-PO: a methacrylate copolymer of ethyl acrylate, methyl methacrylate and a low content of methacrylic acid ester with quaternary ammonium groups: poly(ethyl acrylate-co-methyl methacrylate-co-trimethylammonioethyl methacrylate chloride) 1:2: 0.2 (Evonik Indus. AG, Germany)

EPO: Eudragit® EPO: a cationic methacrylate copolymer based on dimethylaminoethyl methacrylate, butyl methacrylate, and methyl methacrylate: poly(butyl methacrylate-co-(2-demethylaminoeethyl) methacrylate-co-methyl methacrylate) 1:2:1 (Evonik Indus. AG, Germany)

MN30D: Eudragit® NM30D: a methacrylate copolymer based on ethyl acrylate and methyl methacrylate: poly (ethyl acrylate-co-methyl methacrylate) 2:1 (Evonik Indus. AG, Germany)

Referring to Tables 1.1 and 1.2, Example 1 was brittle and exhibited relatively low adhesion (both average force and average area). Modifications to Example 1, shown in Examples 2-13, were undertaken by the present inventors in an effort to develop a formulation having enhanced properties, e.g., increased flexibility, without a loss of other desirable properties, e.g., fenretinide release. These formulations included fenretinide, a transmucosal permeation enhancer comprising PG and menthol, and a methacrylate copolymer, in various amounts, with additional ingredients in varying amounts, e.g., povidone (PVP), citrate ester, and a solubilizer selected from the group consisting of a nonionic surfactant, a bile salt, a phospholipid, a polymeric solubilizer and mixtures thereof. Although the modified formulations in Examples 2-13 exhibited about 2× to about 6× enhancement in average force, and from about 6× to about 40× enhancement in average area, each was classified as "brittle" when tested in accordance with the protocol described below.

In Example 13, the present inventors attempt to enhance the flexibility of the formulation by making certain modifications thereto, e.g., increasing the PG concentration and selecting a methacrylate copolymer having a relatively low glass transition temperature (below 25° C.) in contrast to the methacrylate copolymers used in Desai which had a glass transition temperature above room temperature. It was unexpectedly found that these changes did not provide a formulation film that was flexible, but resulted in a film that was brittle (under the test protocol described herein) with moderate mucoadhesion.

It was surprisingly discovered that the addition of HPC to the formulation provided enhanced flexibility to a fenretinide-containing film. As can be observed from the data in Tables 1.1 and 1.2, formulation films without hydroxypropyl cellulose (HPC) were classified as "brittle" under the test described herein, while formulations including HPC were classified as "flexible" under that same test.

It was further unexpectedly found that the following modifications also contributed to the enhanced flexibility of films prepared from the formulations: a reduction in the PVP content; omission of methacrylate copolymers, and/or a limit on the solubilizer content, with all three being most desirable. Such films also exhibited good mucoadhesion.

It was further surprisingly discovered that a flexible film could be prepared that had a relatively high content of fenretinide, up to about 15 wt. % of the formulation, wherein the film also exhibited good mucoadhesion and remained flexible. As films with relatively lesser amounts of fenretinide were characterized as brittle, it was surprisingly found that the fenretinide concentration in a formulation did not affect the average force of the film prepared therefrom.

In addition, the inclusion of plasticizers (e.g., TEC: TEAC, a 1:1 weight ratio) in the absence of HPC was not found to provide a formulation film that was flexible (as described herein). However, when HPC is present in the formulation, Tables 1.1 and 1.2 also support the criticality of the TEAC: TEC weight ratio, wherein data in these tables show that a 3:1 TEAC to TEC weight ratio provides a surprising improvement in mucoadhesion as measured in accordance with the methodology described herein, despite TEAC possessing a relatively higher hydrophobic (soluble 1 in 140 of water) molecular structure compared to TEC (soluble 1 in 15 of water) molecular structure.

Of further interest were formulations without fenretinide, i.e., Examples 17 and 18. These formulation films were flexible, but exhibited phase separation in the form of an oily substance on the surface of the film. Thus, it was unexpectedly discovered that fenretinide performs what may be referred to as a compatibility function relative to the other film ingredients.

A correlation also was surprisingly found between a film that was deemed flexible and the ability to prepare individual dosage forms from such flexible film. Generally, it was found that a formulation film deemed flexible when folded over onto itself (as described above) would also be able to withstand a die-cutting process without damaging (e.g., cracking, chipping) of the film.

Example 2

This example provides data on the extent to which fenretinide diffuses into and through human skin.

A series of five (5) fenretinide-containing films of differing formulations (i.e., the formulations described in Examples 14 (tested twice), 16, 22 and 23 of Tables 1.1 and 1.2) were prepared in accordance with the methodology described in Example 1, wherein the formulation had a surface area of 1.039 cm$^2$. The formulations were tested as follows.

Fenretinide Permeation and Tissue Recovery

Frozen, posterior torso, split-thickness human cadaver skin was received and utilized upon thawing. Tissues samples were cut to size for mounting onto upright 8 mL Franz diffusion cells and allowed to equilibrate for one hour, with the dermis side of each skin contacting temperature-controlled (32.5° C.) 1% Tween aqueous receiver media during that one hour period.

After the expiration of this one hour period, 25 μL DPBS (Dulbecco's phosphate-buffered saline) was pipetted onto the center of each tissue, followed by application of one 1.039 cm$^2$ unit of the formulation film to be tested onto the wetted tissue surface. 25 μL DPBS was then pipetted onto the upper (non-skin contacting) surface of the formulation film. The Franz cell was capped with a donor cover and the Franz cell was brought to 8.0 mL volume with fresh receiver media. Six such Franz cells were prepared for each formulation film that was tested.

For each formulation film being analyzed, tissue samples were removed from three of the six Franz cells after 30 minutes (post-capping) with the remaining three tissue samples being removed from the other three Franz cells after 6 hours (post-capping). For the latter three Franz cells, media was removed from each Franz cell at time points at 0.5, 1.0, 2.0, 4.0, and 6.0 hours, and replaced with a fresh volume of receiver media until the next specified sampling time. The receiver media sample obtained thereby was transferred to HPLC vials and analyzed via UPLC/UV.

After each tissue sample was removed from the Franz cell, it was wiped dry with a Kimwipe to remove any residual formulation, and then placed into a 1.5 mL centrifuge tube. The tissues were then extracted in DMSO and ethanol to recover the fenretinide in the tissue, with the extracted liquid being analyzed to determine the amount of fenretinide therein (and, thus, to assess the amount of fenretinide that had passed from the formulation film into the tissue at the particular time point).

Table 2 reports data on the average quantity of fenretinide recovered from human cadaver skin (n=2) after 30 minutes of exposure.

unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "illustrative," "such as") provided herein, is intended merely to better illuminate the invention and does not pose a limitation on the scope of the invention unless otherwise claimed. No language in the specification should be construed as indicating any non-claimed element as essential to the practice of the invention.

TABLE 2

| Formula (Tables 1.1 and 1.2) | Assay (μg Fenretinide) | Avg. Recovery (μg Fenretinide) | % Fenretinide Recovered in Tissue | Stand Dev. | % RSD | 4-HPR (μM) |
|---|---|---|---|---|---|---|
| Ex. 14 | 2413 | 14.53 | 0.60 | 7.67 | 52.8 | 37.11 |
| Ex. 16 | 2577 | 5.40 | 0.21 | 0.02 | 0.4 | 13.79 |
| Ex. 23 | 2920 | 3.53 | 0.12 | 0.43 | 12.2 | 9.02 |
| Ex. 22 | 2790 | 7.03 | 0.25 | 4.88 | 69.4 | 17.95 |
| Ex. 14 | 2413 | 7.20 | 0.30 | 2.81 | 39.0 | 18.39 |

The concentration of fenretinide reported in Table 2 (4-HPR (μM)) is based upon the amount of fenretinide that was extracted from 25 mg (average tissue weight) and that was quantified by the UPLC analytical method (reported as mg/mL), converted from mg/mL to μmoles/mL using the MW of fenretinide (391.55), then converting from μmoles/mL to μM by multiplying μmoles by 1000 to convert to μmoles/L (μM).

No fenretinide was detected in the Franz cell media samples even after the formulation film was in contact with the cadaver skin for 6 hours. This indicates that fenretinide diffuses into the skin but does not diffuse through the skin, and that the formulation films thus do not present a risk for systemic circulation of fenretinide.

The weight percent of the ingredients in the formulations described herein should be understood to be based on the total weight of a fenretinide-containing film excluding any volatile ingredients (e.g., acetone, isopropanol, ethanol) from the formulation that are used to in the preparation of the film.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, Although preferred embodiments of this invention are described herein, variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

I claim:
1. A formulation comprising:
   (a) about 10 wt. % to about 20 wt. % fenretinide;
   (b) about 6 wt. % to about 9 wt. % propylene glycol;
   (c) about 12 wt. % to about 18 wt. % menthol;
   (d) about 20 wt. % to about 25 wt. % polyvinyl pyrrolidone;
   (e) about 3 wt. % to about 8 wt. % triethyl citrate;
   (f) about 10 wt. % to about 20 wt. % triethyl-2-acetylcitrate; and
   (g) about 15 wt. % to about 25 wt. % hydroxypropyl cellulose,
   wherein the weight percents are based on the total weight of the formulation excluding any volatile ingredients.

2. The formulation according to claim 1, wherein the formulation comprises:

(a) about 15 wt. % fenretinide;

(b) about 7.5 wt. % propylene glycol;

(c) about 15 wt. % menthol;

(d) about 20 wt. % polyvinyl pyrrolidone;

(e) about 5 wt. % triethyl citrate;

(f) about 15 wt. % triethyl-2-acetylcitrate;

(g) about 20 wt. % hydroxypropyl cellulose; and (h) about 2.5 wt. % of a nonionic surfactant;

wherein the weight percent of each ingredient in the formulation is based on the total weight of the formulation excluding any volatile ingredients.

3. The formulation according to claim 2, wherein the formulation is in the form of a film.

4. The formulation according to claim 3, wherein the film has an average thickness of about 0.1 mm to about 0.2 mm.

5. A mucoadhesive delivery system comprising:

(a) a backing layer, and (b) a formulation comprising:

(i) about 10 wt. % to about 20 wt. % fenretinide;

(ii) about 6 wt. % to about 9 wt. % propylene glycol;

(iii) about 12 wt. % to about 18 wt. % menthol;

(iv) about 20 wt. % to about 25 wt. % polyvinyl pyrrolidone;

(v) about 3 wt. % to about 8 wt. % triethyl citrate;

(vi) about 10 wt. % to about 20 wt. % triethyl-2-acetylcitrate; and (v) about 15 wt. % to about 25 wt. % hydroxypropyl cellulose, wherein the weight percents are based on the total weight of the formulation excluding any volatile ingredients.

6. The system of claim 5, wherein the formulation comprises:

(i) about 15 wt. % fenretinide;

(ii) about 7.5 wt. % propylene glycol;

(iii) about 15 wt. % menthol;

(iv) about 20 wt. % polyvinyl pyrrolidone;

(v) about 5 wt. % triethyl citrate;

(vi) about 15 wt. % triethyl-2-acetylcitrate, (vii) about 20 wt. % hydroxypropyl cellulose; and (viii) about 2.5 wt. % of a nonionic surfactant;

wherein the weight percent of each ingredient in the formulation is based on the total weight of the formulation excluding any volatile ingredients.

7. The system of claim 6, wherein the formulation is in the form of a film having a thickness of about 0.1 mm to about 0.2 mm.

26

8. A formulation consisting of:

(a) about 15 wt. % fenretinide;

(b) about 7.5 wt. % propylene glycol;

(c) about 15 wt. % menthol;

(d) about 20 wt. % polyvinyl pyrrolidone;

(e) about 5 wt. % triethyl citrate;

(f) about 15 wt. % triethyl-2-acetylcitrate;

(g) about 20 wt. % hydroxypropyl cellulose; and (h) about 2.5 wt. % of a nonionic surfactant;

wherein the weight percent of each ingredient in the formulation is based on the total weight of the formulation excluding any volatile ingredients.

9. A mucoadhesive delivery system comprising:

(a) a backing layer, and (b) a formulation consisting of:

(i) about 10 wt. % to about 20 wt. % fenretinide;

(ii) about 6 wt. % to about 9 wt. % propylene glycol;

(iii) about 12 wt. % to about 18 wt. % menthol;

(iv) about 20 wt. % to about 25 wt. % polyvinyl pyrrolidone;

(v) about 3 wt. % to about 8 wt. % triethyl citrate;

(vi) about 10 wt. % to about 20 wt. % triethyl-2-acetylcitrate;

(vii) about 15 wt. % to about 25 wt. % hydroxypropyl cellulose; and (viii) about 2.5 wt. % of a nonionic surfactant;

wherein the weight percents are based on the total weight of the formulation excluding any volatile ingredients.

10. The composition of claim 1, wherein the hydroxypropyl cellulose in the formulation has an average MW of about 200,000 to about 300,000.

11. A method for the treatment of a patient afflicted with a precancerous lesion in the stratified squamous epithelium of mucosal tissue comprising:

a) Providing the mucoadhesive delivery system of claim 1;

b) Applying the formulation onto the precancerous lesion.

12. The method of claim 11, wherein the formulation is applied onto the precancerous lesion for between about 1 and about 60 minutes.

13. The method of claim 12, wherein the formulation is applied onto the lesion at least once per week for between 1 and 12 weeks.

14. The method of claim 11, wherein the hydroxypropyl cellulose in the formulation has an average MW of about 200,000 to about 300,000.

15. The method of claim 11, wherein the formulation is in the form of a film.

16. The method of claim 15, wherein the film has an average thickness of about 0.1 mm to about 0.2 mm.

* * * * *